(12) United States Patent
Brtko et al.

(10) Patent No.: US 8,076,508 B2
(45) Date of Patent: Dec. 13, 2011

(54) PREPARATION OF ACETIC ACID

(75) Inventors: Wayne J. Brtko, Glen Mills, PA (US); Michael E. Fitzpatrick, League City, TX (US)

(73) Assignee: Lyondell Chemical Technology, Houston, TX (US)

( * ) Notice: Subject to any disclaimer, the term of this patent is extended or adjusted under 35 U.S.C. 154(b) by 412 days.

(21) Appl. No.: 12/315,887

(22) Filed: Dec. 8, 2008

(65) Prior Publication Data

US 2010/0145097 A1    Jun. 10, 2010

(51) Int. Cl.
*C07C 51/12* (2006.01)
(52) U.S. Cl. ........................................ 562/519
(58) Field of Classification Search .................. None
See application file for complete search history.

(56) References Cited

U.S. PATENT DOCUMENTS

| | | | |
|---|---|---|---|
| 5,817,869 A | 10/1998 | Hinnenkamp et al. | |
| 5,932,764 A | 8/1999 | Morris et al. | |
| 5,990,347 A | 11/1999 | Clode | |
| 6,031,129 A | 2/2000 | Hinnenkamp et al. | |
| 6,153,792 A | 11/2000 | Leet et al. | |
| 6,552,221 B1 * | 4/2003 | Hallinan et al. | 562/519 |
| 7,208,625 B1 | 4/2007 | Wang et al. | |
| 7,345,197 B1 | 3/2008 | Hallinan et al. | |
| 7,390,919 B1 | 6/2008 | Salisbury et al. | |

FOREIGN PATENT DOCUMENTS

| | | |
|---|---|---|
| EP | 0535825 A2 * | 9/1992 |
| EP | 0 535 825 A2 | 7/1993 |
| EP | 0 573 189 A1 | 8/1993 |

OTHER PUBLICATIONS

White et al, Basic Energy Sciences Advisory Committee Subpanel Workshop Report, Opportunities for Catalysis in the 21st Century, 2002, pp. 1-47.*

* cited by examiner

*Primary Examiner* — Paul A Zucker

(57) ABSTRACT

A process for producing acetic acid is disclosed. The process comprises carbonylating methanol to form a reaction mixture and flashing the reaction mixture to form a vapor stream and a liquid stream. The flash tank is equipped with a distillation column. The vapor stream comprises acetic acid and other volatile components but essentially no catalyst. The liquid stream comprises the catalyst and sufficient amounts of water and acetic acid to carry and stabilize the catalyst. The liquid stream is recycled to the carbonylation and the vapor stream is subjected to further separation to produce essentially pure acetic acid.

20 Claims, 2 Drawing Sheets

PREPARATION OF ACETIC ACID

FIELD OF THE INVENTION

The invention relates to the preparation of acetic acid by methanol carbonylation. More particularly, the invention relates to an acetic acid production process which has reduced catalyst loss.

BACKGROUND OF THE INVENTION

Production of acetic acid by methanol carbonylation is known. See U.S. Pat. No. 5,817,869. In the current acetic acid production process, a reaction mixture is withdrawn from the reactor and is separated by a flash tank into a liquid fraction comprising the catalyst and the catalyst stabilizer and a vapor fraction comprising the acetic acid product, methanol, carbon dioxide, water, methyl iodide, and impurities generated during the carbonylation reaction. The liquid fraction is then recycled to the carbonylation reactor. The vapor fraction is passed to a so-called "light-ends distillation." The light-ends distillation separates acetic acid from other components and produces a crude acetic acid product. The crude acetic acid product is passed to a drying column to remove water and then is subjected to a so called "heavy-ends distillation" to remove the heavy impurities such as propionic acid.

In the current process, the flash tank does not have a distillation column for the vapor-liquid separation. Thus, the catalyst can be entrained into the flash vapor stream. Deposits of solid catalyst have been seen in downstream equipment. Even though the majority of this catalyst is recovered when cleaning during major shutdowns, major shutdowns are usually three years apart. In the interim, process equipment becomes catalyst inventory storage equipment. Additionally, as catalyst plates out in downstream equipment, it must be replaced upstream with fresh catalyst.

Thus, a new process for producing acetic acid is needed. Ideally, the process reduces the catalyst entrainment in the vapor stream from the flash tank.

SUMMARY OF THE INVENTION

The invention is a process for producing acetic acid. The process comprises carbonylating methanol in the presence of a catalyst to form a reaction mixture and flashing the reaction mixture in a flash tank equipped with a distillation column. The vapor stream from the flash tank distillation column comprises acetic acid and other volatile components but essentially no catalyst. The liquid stream comprises the catalyst. The liquid stream is recycled to the carbonylation. The vapor stream is subjected to further separation to produce an essentially pure acetic acid product. The process of the invention reduces or eliminates the catalyst entrainment in the vapor stream and limits the catalyst from being carried over to downstream equipment.

DETAILED DESCRIPTION OF THE INVENTION

Figure 1:
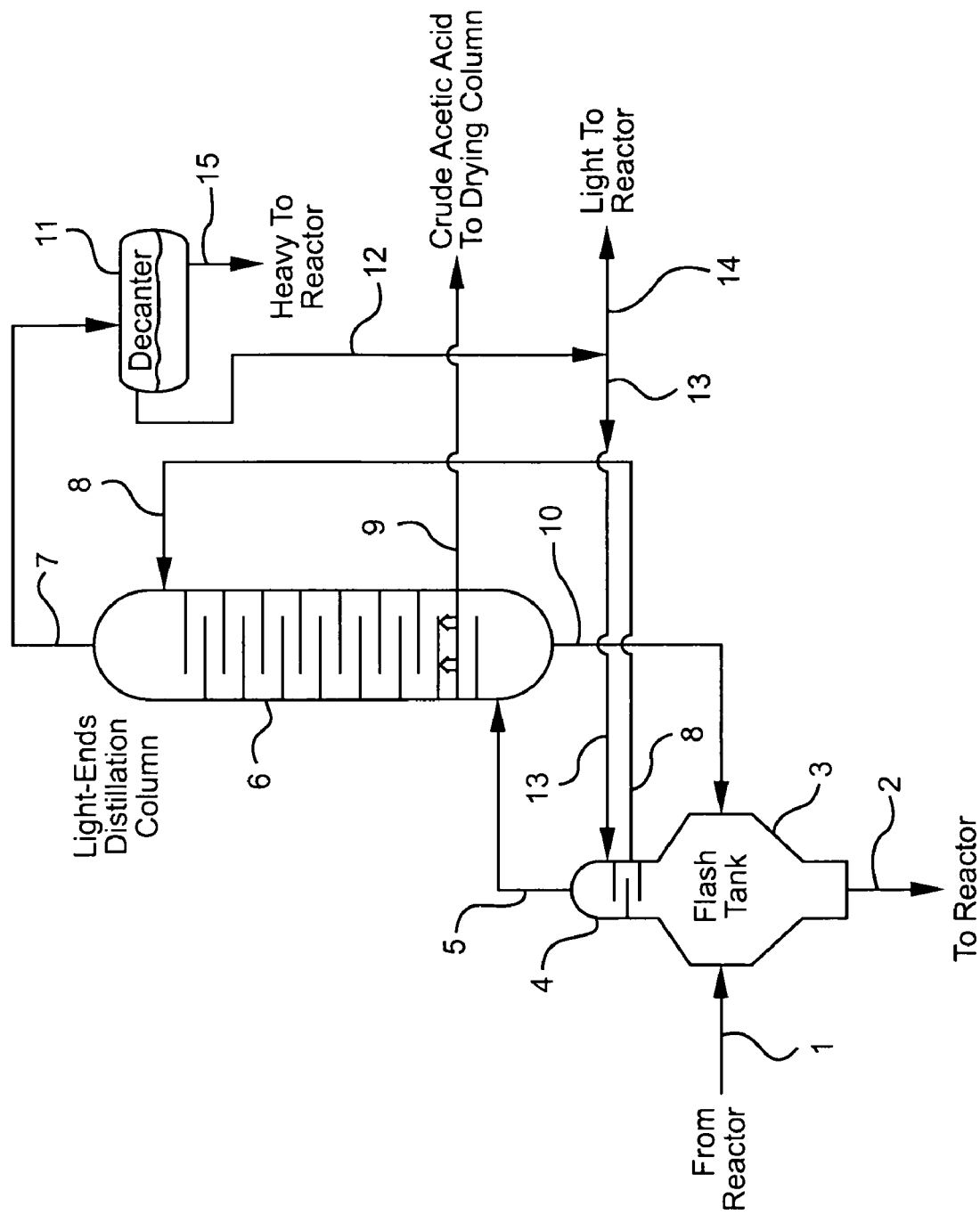
FIG. 1 is an illustrative flow diagram of an embodiment of the process of the invention.

The process of the invention comprises carbonylating methanol. The carbonylation reaction is performed in the presence of a catalyst. Suitable catalysts include those known in the acetic acid industry. Examples of suitable carbonylation catalysts include rhodium catalysts and iridium catalysts. Suitable rhodium catalysts are taught, for example, by U.S. Pat. No. 5,817,869. Suitable rhodium catalysts include rhodium metal and rhodium compounds. Preferably, the rhodium compounds are selected from the group consisting of rhodium salts, rhodium oxides, rhodium acetates, organo-rhodium compounds, coordination compounds of rhodium, the like, and mixtures thereof. More preferably, the rhodium compounds are selected from the group consisting of $Rh_2(CO)_4I_2$, $Rh_2(CO)_4Br_2$, $Rh_2(CO)_4Cl_2$, $Rh(CH_3CO_2)_2$, $Rh(CH_3CO_2)_3$, $[H]Rh(CO)_2I_2$, the like, and mixtures thereof. Most preferably, the rhodium compounds are selected from the group consisting of $[H]Rh(CO)_2I_2$, $Rh(CH_3CO_2)_2$, the like, and mixtures thereof. Suitable iridium catalysts are taught, for example, by U.S. Pat. No. 5,932,764. Suitable iridium catalysts include iridium metal and iridium compounds. Examples of suitable iridium compounds include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_4I_2]^-H^+$, $[Ir(CO)_2Br_2]^-H^+$, $[IR(CO)_2I_2]^-H^+$, $[Ir(CH_3)I_3(CO)_2]^-H^+$, $Ir_4(CO)_{12}$, $IrCl_3 \cdot 4H_2O$, $IrBr_3 \cdot 4H_2O$, $Ir_3(CO)_{12}$, $Ir_2O_3$, $IrO_2$, $Ir(acac)(CO)_2$, $Ir(acac)_3$, $Ir(OAc)_3$, $[Ir_3O(OAc)_6(H_2O)_3][OAc]$, and $H_2[IrCl_6]$. Preferably, the iridium compounds are selected from the group consisting of acetates, oxalates, acetoacetates, the like, and mixtures thereof. More preferably, the iridium compounds are acetates. The iridium catalyst is preferably used with a co-catalyst. Preferred co-catalysts include metals and metal compounds selected from the group consisting of osmium, rhenium, ruthenium, cadmium, mercury, zinc, gallium, indium, and tungsten, their compounds, the like, and mixtures thereof. More preferred co-catalysts are selected from the group consisting of ruthenium compounds and osmium compounds. Most preferred co-catalysts are ruthenium compounds. Preferably, the co-catalysts are acetates.

The carbonylation reaction is preferably performed in the presence of a catalyst stabilizer. Suitable catalyst stabilizers include those known to the industry. In general, there are two types of catalyst stabilizers. The first type of catalyst stabilizer is metal iodide salt such as lithium iodide. The second type of catalyst stabilizer is a non-salt stabilizer. Preferred non-salt stabilizers are pentavalent Group VA oxides. See U.S. Pat. No. 5,817,869. Phosphine oxides are more preferred. Triphenylphosphine oxides are most preferred.

The carbonylation reaction is preferably performed in the presence of water. Preferably, the concentration of water present is from about 2 wt % to about 14 wt % based on the total weight of the reaction medium. More preferably, the water concentration is from about 2 wt % to about 10 wt %. Most preferably, the water concentration is from about 4 wt % to about 8 wt %.

The carbonylation reaction is preferably performed in the presence of methyl acetate. Methyl acetate can be formed in situ. If desirable, methyl acetate can be added as a starting material to the reaction mixture. Preferably, the concentration of methyl acetate is from about 2 wt % to about 20 wt % based on the total weight of the reaction medium. More preferably, the concentration of methyl acetate is from about 2 wt % to about 16 wt %. Most preferably, the concentration of methyl acetate is from about 2 wt % to about 8 wt %. Alternatively, methyl acetate or a mixture of methyl acetate and methanol from byproduct streams of the methanolysis of polyvinyl acetate or ethylene-vinyl acetate copolymers can be used for the carbonylation reaction.

The carbonylation reaction is preferably performed in the presence of methyl iodide. Methyl iodide is a catalyst promoter. Preferably, the concentration of methyl iodide is from about 0.6 wt % to about 36 wt % based on the total weight of the reaction medium. More preferably, the concentration of methyl iodide is from about 4 wt % to about 24 wt %. Most preferably, the concentration of methyl iodide is from about 6 wt % to about 20 wt %. Alternatively, methyl iodide can be generated in the carbonylation reactor by adding hydrogen iodide (HI).

Methanol and carbon monoxide are fed to the carbonylation reactor. The methanol feed to the carbonylation reaction can come from a syngas-methanol facility or any other source. Methanol does not react directly with carbon monoxide to form acetic acid. It is converted to methyl iodide by the hydrogen iodide present in the acetic acid reactor and then reacts with carbon monoxide and water to give acetic acid and regenerate the hydrogen iodide. Carbon monoxide not only becomes part of the acetic acid molecule, but it also plays an important role in the formation and stability of the active catalyst.

The carbonylation reaction is preferably performed at a temperature within the range of about 150° C. to about 250° C. More preferably, the reaction is performed at a temperature within the range of about 150° C. to about 200° C. The carbonylation reaction is preferably performed under a pressure within the range of about 200 psia (14 kg/cm$^2$) to about 1,000 psia (70 kg/cm$^2$). More preferably, the reaction is performed under a pressure within the range of about 300 psia (21 kg/cm$^2$) to about 500 psia (35 kg/cm$^2$).

The reaction mixture is withdrawn from the reactor and is flashed to form a vapor stream and a liquid stream. The flash tank is equipped with a distillation column. Preferably, the distillation column has at least two trays. More preferably, the distillation column has two to five trays. The vapor stream comprises acetic acid and other volatile components such as methanol, methyl acetate, methyl iodide, carbon monoxide, carbon dioxide, and water, while the liquid stream comprises the catalyst. The liquid stream also comprises sufficient amounts of water and acetic acid to carry and stabilize the catalyst. Non-volatile catalyst stabilizers are preferably in the liquid stream. The liquid stream is recycled to the carbonylation. The vapor stream is subjected to further distillation.

The vapor stream is preferably distilled in a light-ends distillation column to form an overhead stream, a crude acetic acid product stream, and a bottom stream. Preferably, the light-ends distillation column has at least 10 theoretical stages or 16 actual stages. More preferably, the distillation column has at least 14 theoretical stages. Most preferably, the distillation column has at least 18 theoretical stages. One actual stage equals approximately to 0.6 theoretical stage. Actual stages can be trays or packing. The reaction mixture is fed to the light-ends distillation column at the bottom or the first stage of the column. The distillation column is preferably operated at an overhead pressure within the range of 20 psia (1.4 kg/cm$^2$) to 40 psia (2.8 kg/cm$^2$). More preferably, the overhead pressure is within the range of 30 psia (2 kg/cm$^2$) to 35 psia (2.5 kg/cm$^2$). Preferably, the overhead temperature is within the range of 95° C. to 135° C. More preferably, the overhead temperature is within the range of 110° C. to to 135° C. Most preferably, the overhead temperature is within the range of 125° C. to 135° C. The overhead vapor stream preferably comprises water, carbon monoxide, carbon dioxide, methyl iodide, methyl acetate, methanol and acetic acid.

The light-ends distillation column is preferably operated at a bottom pressure within the range of 25 psia (1.8 kg/cm$^2$) to 45 psia (3.2 kg/cm$^2$). More preferably, the bottom pressure is within the range of 30 psia (2.1 kg/cm$^2$) to 40 psia (2.8 kg/cm$^2$). Preferably, the bottom temperature is within the range of 115° C. to 155° C. More preferably, the bottom temperature is within the range of 125° C. to 135° C. The bottom stream preferably comprises acetic acid, methyl iodide, methyl acetate, hydrogen iodide, and water.

The crude acetic acid stream is taken from a liquid sidedraw which is preferably operated at a pressure within the range of 25 psia (1.8 kg/cm$^2$) to 45 psia (3.2 kg/cm$^2$). More preferably, the sidedraw pressure is within the range of 30 psia (2.1 kg/cm$^2$) to 40 psia (2.8 kg/cm$^2$). Preferably, the sidedraw temperature is within the range of 110° C. to 140° C. More preferably, the sidedraw temperature is within the range of 125° C. to 135° C. The sidedraw is preferably taken between the fifth to the eighth actual stage. The crude acetic acid stream preferably comprises acetic acid, water and heavy impurities.

The overhead vapor stream from the light-ends distillation column is preferably condensed and separated in a decanter to a light, aqueous phase and a heavy, organic phase. The heavy, organic phase preferably comprises methyl iodide and methyl acetate. The light, aqueous phase preferably comprises water (greater than 50%), acetic acid, and methyl acetate. In one preferred embodiment, a fraction of the light, aqueous phase is introduced to the top of the flash tank distillation column and a fraction of liquid is taken from the bottom of the flash tank distillation column and is introduced to the top tray of the light-ends distillation column (see FIG. 1). Since reflux to the flash tank distillation column is provided by a portion of the decanter light, aqueous phase which is more readily to carry the catalyst, the catalyst is washed down to the liquid at the bottom of the flash tank. In another preferred embodiment, a portion of crude acetic acid stream is introduced to and refluxes the flash tank distillation column; the crude acetic acid washes the catalyst from the vapor stream down to the bottom liquid of the flash tank (see FIG. 2).

The crude acetic acid stream is optionally subjected to further purification such as drying-distillation to remove water and heavy-ends distillation to remove heavy impurities such as propionic acid.

The following examples merely illustrate the invention. Those skilled in the art will recognize many variations that are within the spirit of the invention and scope of the claims.

EXAMPLE 1

This process of the invention is modeled by Aspen Plus and the results are given below for two examples.

As shown in FIG. 1, a carbonylation mixture 1 (100 parts by weight) comprising water 6.48%, carbon monoxide 0.14%, carbon dioxide 0.07%, hydrogen iodide 2.98%, methyl iodide 12.64%, methyl acetate 2.87%, methanol 0.02%, acetic acid 64.72%, propionic acid 0.04%, a catalyst stabilizer 10.0%, and a catalyst 0.04% is flashed across a valve into a flash tank 3. A recycle stream 10 from the light-ends distillation column 6 (0.2 parts by weight) is also fed to the flash tank 3.

The flash tank distillation column 4 is installed on top of the flash tank 3 and contains two trays. A portion 13 (12.1 parts by weight) of the decanter light phase liquid 12 is fed to the top tray as reflux. The remainder 14 is recycled to the reactor. The flash tank distillation trays overhead operates at 35 psia (2.3 kg/cm$^2$) and 131.4° C. The overhead vapor stream 5 (26.1 parts by weight) is fed to the downstream light-ends distillation column 6 at bottom stage 1. Flash tank bottoms 2 (69.8 parts by weight) are recycled to the reactor. The bottom liquid 8 from the distillation column is taken as a sidedraw (16.5 parts by weight) and sent to the light-ends distillation column 6 as reflux.

The light-ends distillation column 6 has 10 theoretical stages or 16 actual stages. The overhead is at 34 psia (2.4 kg/cm$^2$) and 130.7° C. The overhead stream 7 (26.9 parts by weight) comprises water 9.8%, carbon monoxide 0.5%, carbon dioxide 0.3%, methyl iodide 32.3%, methyl acetate 7.0%, methanol 0.1% and acetic acid 50.0%. The overhead stream 7 is cooled to 38° C. and condensate flows to a decanter 11 for liquid separation.

The light-ends distillation column bottom operates at 33.7 psia (2.4 kg/cm$^2$) and 129.9° C. The bottom stream 10 (0.2 parts by weight) comprises water 10.34%, hydrogen iodide 0.03%, methyl iodide 20.66%, methyl acetate 1.87%, methanol 0.02%, acetic acid 67.02%, propionic acid 0.03% and catalyst stabilizer 0.03%. This is the stream that recycles to the flash tank 3.

A liquid sidedraw 9 (15.5 parts by weight) at 33.7 psia (2.4 kg/cm$^2$) and 130° C. is taken from the tray above the bottom tray of the light-ends distillation column. This stream comprises water 10.21%, carbon monoxide 0.002%, carbon dioxide 0.008%, hydrogen iodide 0.16%, methyl iodide 20.22%, methyl acetate 1.89%, methanol 0.02%, acetic acid 67.46% and propionic acid 0.03%. This stream is a crude acetic acid which flows to downstream equipment for drying and recovery of pure acetic acid.

EXAMPLE 2

Figure 2:
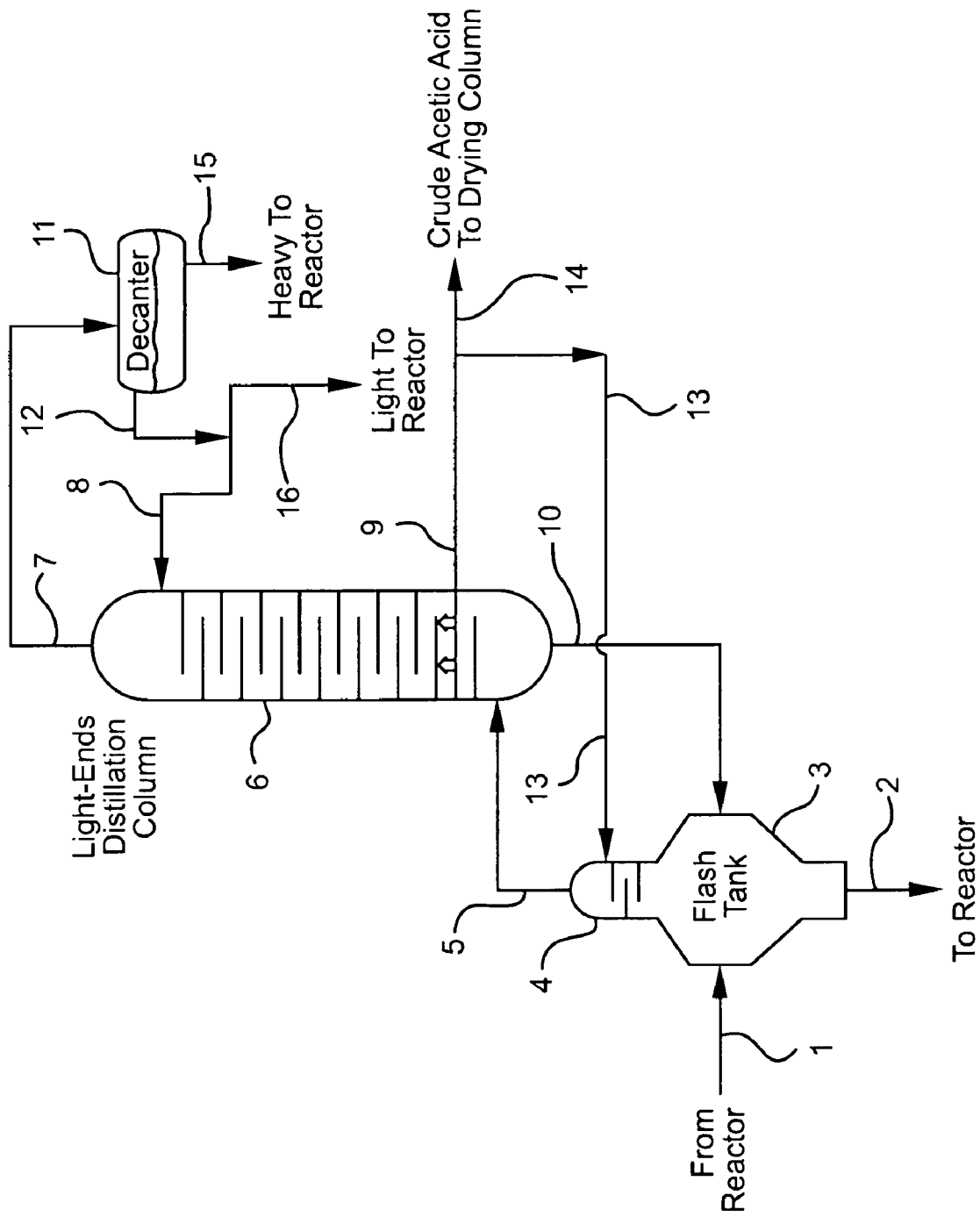
FIG. 2 is an illustrative flow diagram of another embodiment of the process of the invention.

As shown in FIG. 2, a carbonylation mixture 1 (100 parts by weight) comprising water 6.48%, carbon monoxide 0.14%, carbon dioxide 0.07%, hydrogen iodide 2.98%, methyl iodide 12.64%, methyl acetate 2.87%, methanol 0.02%, acetic acid 64.72%, propionic acid 0.04%, a catalyst stabilizer 10.0%, and a catalyst 0.04% is flashed across a valve into a flash tank 3. One recycle stream 10 from the light-ends distillation column 6 (1.0 parts by weight) is also fed to the flash tank 3.

The flash tank distillation column 4 contains two trays and is installed on top of the flash tank 3. A portion 13 (15.5 parts by weight) of the crude acetic acid liquid stream 9 from light-ends distillation 6 is fed to the top tray as reflux. The remainder 14 is sent to down stream purification (drying distillation and/or heavy-ends distillation). The flash tank distillation trays overhead operates at 35.1 psia (2.5 kg/cm$^2$) and 129.7° C. The overhead vapor 5 (25.0 parts by weight) is fed to the downstream light-ends distillation column 6 at bottom stage 1. Flash tank bottoms 2 (71.5 parts by weight) are recycled to the reactor and liquid (9.3 parts by weight) from the bottom tray of the flash tank distillation drains into the flash tank 3.

The light-ends distillation column 6 has 10 theoretical stages or 16 actual stages. The distillation column overhead operates at 33.7 psia (2.4 kg/cm$^2$) and 124.2° C. The overhead vapor 7 (13.5 parts by weight) comprises water 16.6%, carbon monoxide 1.0%, carbon dioxide 0.6%, methyl iodide 45.7%, methyl acetate 13.4%, methanol 0.8% and acetic acid 21.9%. The overhead vapor 7 is cooled to 38° C. and condensate flows to a decanter 11 for liquid separation.

The light-ends distillation column bottom operates at 33.7 psia (2.4 kg/cm$^2$) and 128° C. The bottom stream 10 (1 part by weight) comprises water 8.37%, hydrogen iodide 0.11%, methyl iodide 28.64%, methyl acetate 1.69%, methanol 0.01%, acetic acid 61.12%, propionic acid 0.03% and catalyst stabilizer 0.03%. This stream recycles to the flash tank 3. A liquid sidedraw 9 (16.3 parts by weight) at 33.7 psia (2.4 kg/cm$^2$) and 127.3° C. is taken from the tray above the bottom tray of the light-ends distillation column. This stream comprises water 9.66%, carbon monoxide 0.003%, carbon dioxide 0.008%, hydrogen iodide 0.02%, methyl iodide 33.94%, methyl acetate 1.52%, methanol 0.009%, acetic acid 54.82% and propionic acid 0.02%. The majority (95%) 14 of the stream 9 is a crude acetic acid which flows to downstream equipment for drying and recovery of pure acetic acid. The remainder (5%) 13 of stream 9 refluxes the trays on top of the flash tank.

As indicated above, Example 1 gives more pure crude acetic acid product than Example 2.

We claim:

1. A process for producing acetic acid, comprising:
   (a) carbonylating methanol in the presence of a carbonylation catalyst to form a reaction mixture;
   (b) flashing and distilling the reaction mixture in a flash tank equipped with a distillation column to form a liquid stream comprising the catalyst at the bottom of the flash tank and a vapor stream at the top of the distillation column; and
   (c) recycling the liquid stream to step (a),
wherein the vapor stream is distilled in a light-ends distillation column to form a bottom stream, a crude acetic acid stream, and an overhead vapor stream,
the overhead vapor stream is condensed and separated into a light phase and a heavy phase, and
a fraction of the light phase is introduced to the top of the flash tank distillation column and a liquid stream is taken from the bottom of the flash tank distillation column and sent to the top of the light-ends distillation column.

2. The process of claim 1, wherein the flash tank distillation column has at least two trays.

3. The process of claim 1, wherein the catalyst is selected from the group consisting of rhodium catalysts and iridium catalysts.

4. The process of claim 1, wherein the catalyst is a rhodium catalyst.

5. The process of claim 1, wherein the bottom stream is recycled to the carbonylation or to the flash tank.

6. The process of claim 1, wherein the crude acetic acid stream is distilled in a drying column and in a heavy-ends distillation column to produce purified acetic acid.

7. The process of claim 4, wherein the catalyst comprises a stabilizer selected from the group consisting of pentavalent Group VA oxides, metal iodide salts, and mixtures thereof.

8. The process of claim 7, wherein the stabilizer is a phosphine oxide.

9. The process of claim 8, wherein the stabilizer is triphenylphosphine oxide.

10. The process of claim 7, wherein the stabilizer is lithium iodide.

11. A process for producing acetic acid, comprising:
    (a) carbonylating methanol in the presence of a carbonylation catalyst to form a reaction mixture;
    (b) flashing and distilling the reaction mixture in a flash tank equipped with a distillation column to form a liquid stream comprising the catalyst at the bottom of the flash tank and a vapor stream at the top of the distillation column; and
    (c) recycling the liquid stream to step (a),
wherein the vapor stream is distilled in a light-ends distillation column to form a bottom stream, a crude acetic acid stream, and an overhead vapor stream,
the overhead vapor stream is condensed and separated into a light phase and a heavy phase, and
a fraction of the crude acetic acid stream is sent to the flash tank distillation column.

12. The process of claim 11, wherein the flash tank distillation column has at least two trays.

13. The process of claim 11, wherein the catalyst is selected from the group consisting of rhodium catalysts and iridium catalysts.

14. The process of claim 11, wherein the bottom stream is recycled to the carbonylation or to the flash tank.

15. The process of claim 11, wherein the crude acetic acid stream is distilled in a drying column and in a heavy-ends distillation column to produce purified acetic acid.

16. The process of claim 11, wherein the catalyst is a rhodium catalyst.

17. The process of claim 16, wherein the catalyst comprises a stabilizer selected from the group consisting of pentavalent Group VA oxides, metal iodide salts, and mixtures thereof.

18. The process of claim 17, wherein the stabilizer is a phosphine oxide.

19. The process of claim 18, wherein the stabilizer is triphenylphosphine oxide.

20. The process of claim 17, wherein the stabilizer is lithium iodide.

* * * * *